(12) United States Patent
Saito et al.

(10) Patent No.: US 8,496,630 B2
(45) Date of Patent: Jul. 30, 2013

(54) TRANSENDOSCOPIC MEDICAL INSTRUMENT

(75) Inventors: Tatsuya Saito, Tokyo (JP); Hiroki Shirato, Sapporo (JP); Shigeaki Ogura, Sapporo (JP)

(73) Assignee: Olympus Corporation, Tokyo (JP)

( * ) Notice: Subject to any disclaimer, the term of this patent is extended or adjusted under 35 U.S.C. 154(b) by 1477 days.

(21) Appl. No.: 11/119,472

(22) Filed: Apr. 29, 2005

(65) Prior Publication Data

US 2005/0251111 A1 Nov. 10, 2005

Related U.S. Application Data

(63) Continuation of application No. PCT/JP03/14222, filed on Nov. 7, 2003.

(30) Foreign Application Priority Data

Nov. 8, 2002 (JP) .................................. 2002-325492

(51) Int. Cl.
*A61M 25/00* (2006.01)
*A61M 31/00* (2006.01)
*A61B 6/00* (2006.01)

(52) U.S. Cl.
USPC .............................. 604/264; 604/60; 600/431

(58) Field of Classification Search
USPC .......... 604/164.01, 158, 167.01, 264, 170.03, 604/95.04, 60; 600/414, 431
See application file for complete search history.

(56) References Cited

U.S. PATENT DOCUMENTS

| 3,625,200 | A | | 12/1971 | Muller |
| 5,439,447 | A | * | 8/1995 | Miraki ..................... 604/102.02 |
| 5,791,338 | A | * | 8/1998 | Merchant et al. ........ 128/200.26 |
| 5,899,850 | A | | 5/1999 | Ouchi |
| 6,162,207 | A | | 12/2000 | Ouchi |
| 6,193,717 | B1 | * | 2/2001 | Ouchi ............................. 606/49 |
| 6,210,377 | B1 | * | 4/2001 | Ouchi .......................... 604/264 |
| 6,228,055 | B1 | | 5/2001 | Foerster et al. |
| 6,251,418 | B1 | * | 6/2001 | Ahern et al. .................. 424/423 |
| 6,336,914 | B1 | | 1/2002 | Gillespie, III |
| 6,725,083 | B1 | * | 4/2004 | Burbank et al. .............. 600/431 |

FOREIGN PATENT DOCUMENTS

| EP | 0 704 189 A1 | 4/1996 |
| JP | 10-309284 | 11/1998 |
| JP | 11-42232 | 2/1999 |
| JP | 2001-58009 | 3/2001 |
| JP | 2002-153475 | 5/2002 |
| WO | WO 01/08578 A1 | 2/2001 |

OTHER PUBLICATIONS

Microfilm of Japanese Utility Model Application No. 2-88250 (Japanese UM Application Kokai Publication No. 4-47415, published Apr. 22, 1992).
Supplementary European Search Report dated May 19, 2010.
Date-of-receipt stamped letter to establish the date (Jun. 24, 2010).

* cited by examiner

*Primary Examiner* — Theodore Stigell
*Assistant Examiner* — Jenna Zhang
(74) *Attorney, Agent, or Firm* — Scully, Scott, Murphy & Presser, P.C.

(57) ABSTRACT

There is provided a transendoscopic medical instrument which can insert, remove and latch a plurality of medical items including a flexible guide unit with respect to a transendoscopic sheath which is selectively inserted into a body cavity such as a bronchial branch.

7 Claims, 12 Drawing Sheets

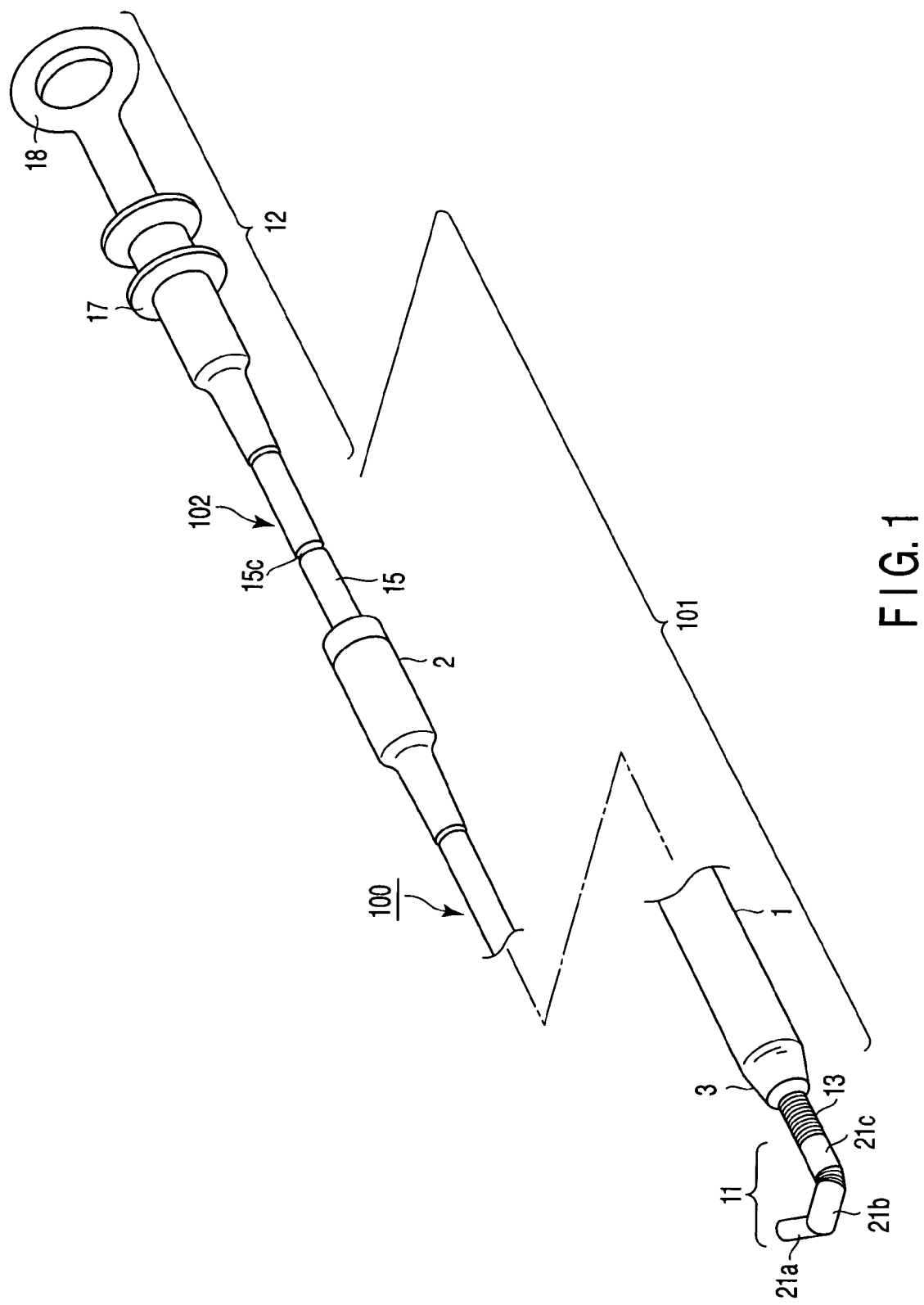
F I G. 1

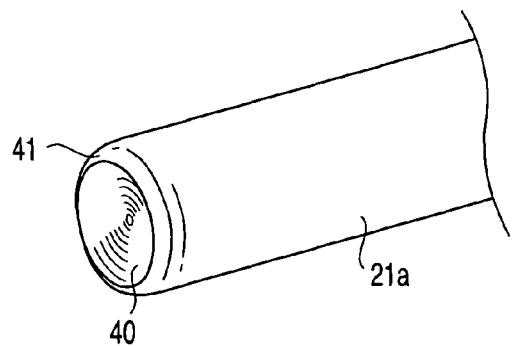
F I G. 21
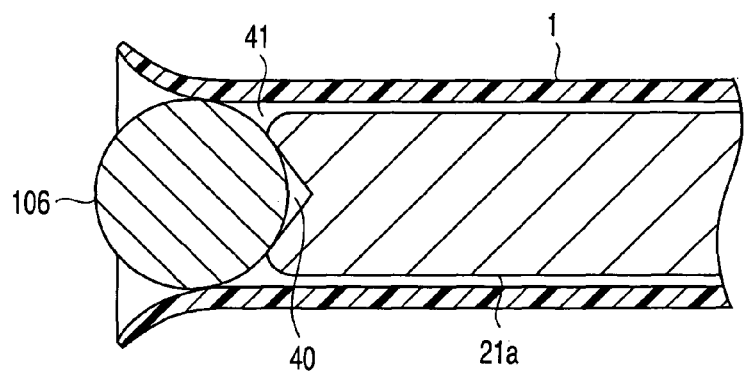
F I G. 22
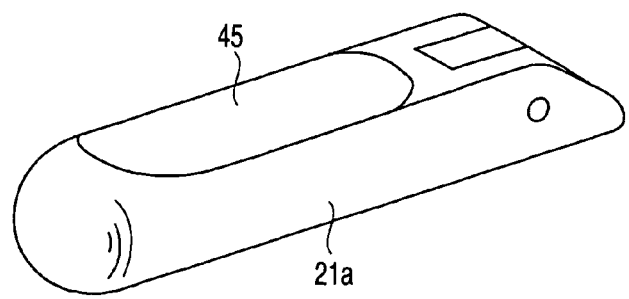
F I G. 23

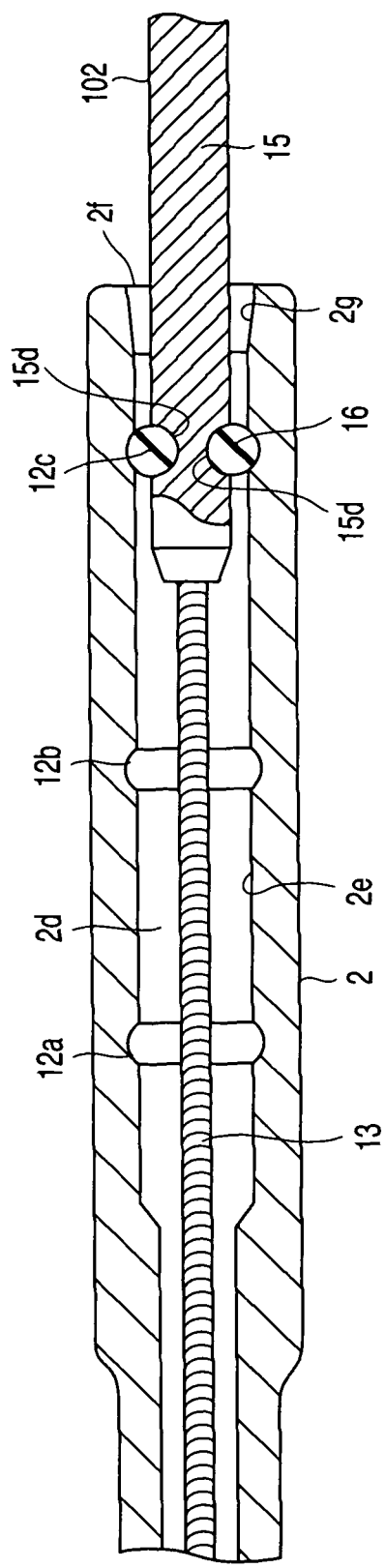
F I G. 27

TRANSENDOSCOPIC MEDICAL INSTRUMENT

CROSS REFERENCE TO RELATED APPLICATIONS

This is a Continuation Application of PCT Application No. PCT/JP03/14222, filed Nov. 7, 2003, which was published under PCT Article 21(2) in Japanese.

This application is based upon and claims the benefit of priority from prior Japanese Patent Application No. 2002-325492, filed Nov. 8, 2002, the entire contents of which are incorporated herein by reference.

BACKGROUND OF THE INVENTION

1. Field of the Invention

The present invention relates to a transendoscopic medical instrument which is used when transendoscopically performing a diagnosis or a therapy.

2. Description of the Related Art

When transendoscopically diagnosing or treating a peripheral bronchial part where complicated branches are deeply formed, a treatment instrument such as a biopsy forceps must be transendoscopically inserted into the peripheral bronchial tube. An approach to the peripheral bronchial tube has been carried out by repeating an insertion operation of a treatment instrument such as a forceps while confirming a current position to which the treatment instrument is inserted using x-rays.

In recent years, patients with peripheral lung cancer have been increased in number, and transendoscopic diagnosis or therapy/treatment is becoming a growing trend. In this case, it is desired to accurately and rapidly approach a transendoscopic forceps or the like intended for a diagnosis, a therapy or the like on the peripheral bronchial tube.

When diagnosing this type of disease, tissue cells are obtained from a peripheral diseased part. Further, in therapies, cases of performing a stereotactic radiosurgery have been recently increased.

Meanwhile, in order to allow a tool for a diagnosis or a therapy of a diseased part of the peripheral bronchial tube to transendoscopically reach a diseased part of the peripheral bronchial tube, a transendoscopic medical instrument is required which is suitable for selecting a bronchial branch and leading the item to the diseased part of the peripheral bronchial tube.

As known from the specification of U.S. Pat. No. 5,791,338, although there is a flexible intubation instrument having an articulated distal end, this intubation instrument is an auxiliary instrument when inserting a tube into a bronchus, and it has a certain degree of rigidity.

On the other hand, an instrument described in the specification of U.S. Pat. No. 6,228,055 is a marking apparatus which embeds a marker element in a tissue, and this is of a type which pushes an end of an insertion portion of a catheter through a tissue and embeds a marker element.

An intubation instrument described in the specification of U.S. Pat. No. 5,791,338 has a flexible articulated distal end.

Furthermore, a marking apparatus described in the specification of U.S. Pat. No. 6,228,055 pushes an end of an insertion portion of a catheter through a tissue and embeds a marker element in this tissue.

BRIEF SUMMARY OF THE INVENTION

According to the present invention, there is provided a transendoscopic medical instrument comprising: a sheath configured to be inserted into a channel of an endoscope; a plurality of types of insertion instruments configured to be inserted into and removed from the sheath; and a latch portion which latches at least one of the insertion instruments inserted in the sheath with respect to the sheath, and is provided to the sheath.

According to the present invention, there is provided a transendoscopic medical instrument comprising: a sheath which can be inserted into a channel of an endoscope; a first insertion instrument which can be inserted into and removed from the sheath; and a latch portion which latches either a second insertion instrument which can be inserted into and removed from the sheath and is different from the first insertion instrument or the first insertion instrument with respect to the sheath, and is provided to the sheath.

According to the present invention, there is provided a transendoscopic medical instrument comprising: a sheath configured to be inserted into a channel of an endoscope; a guide unit which can be inserted into and removed from the sheath and has at an end a flexure portion configured to be flexibly operated by flexural operating means; an insertion instrument which can be inserted into and removed from the sheath and is different from the guide unit; and a latch portion which latches the guide unit inserted in the sheath with respect to the sheath, and is provided to the sheath.

According to the present invention, there is provided a transendoscopic medical instrument comprising: a sheath which can be inserted into a channel of an endoscope and has an end opening portion having at least an inside diameter tapered at an end portion, an x-ray marker member formed of a radiopaque material being able to be arranged in the end portion, the x-ray marker member being latched at the end opening portion at the time of no load, the x-ray marker member being discharged from the end opening portion when a predetermined pushing force is applied; a guide unit configured to be inserted into and removed from the sheath and has an end portion which can push the x-ray marker member when inserted into the sheath and is retractable from the end opening portion of the sheath, and a flexure portion which is operated by flexure operating means and can change a direction of the end portion; and latching means which latches the guide unit with respect to the sheath and is provided to the transendoscopic sheath.

According to the present invention, there is provided a transendoscopic medical instrument comprising: a sheath configured to be inserted into and removed from a channel of an endoscope and into which a plurality of types of insertion instruments can be individually removably inserted; and latching means configured to latch to at least one of the insertion instruments inserted in the sheath and position the insertion instrument with respect to the sheath.

BRIEF DESCRIPTION OF THE SEVERAL VIEWS OF THE DRAWING

FIG. 1 is a perspective view showing an entire transendoscopic medical instrument according to a first embodiment of the present invention;

FIG. 21 is a perspective view of an end acting portion in a guide unit of a transendoscopic medical instrument according to a third embodiment of the present invention;

FIG. 22 is a vertical cross-sectional view of the end portion in the guide unit of the transendoscopic medical instrument according to the third embodiment;

FIG. 23 is a perspective view of an end acting portion in a guide unit of a transendoscopic medical instrument according to a fourth embodiment of the present invention;

FIG. 27 is a vertical cross-sectional view of a hand portion of the transendoscopic medical instrument according to the fifth embodiment of the present invention.

DETAILED DESCRIPTION OF THE INVENTION

First Embodiment

An endoscope guide catheter as a transendoscopic medical instrument according to a first embodiment of the present invention will now be described with reference to FIGS. 1 to 18.

A guide catheter 100 according to this embodiment comprises a mantle tube unit 101 and a guide unit 102. As shown in FIG. 1, an insertion portion of the guide unit 102 is inserted into the mantle tube unit 101, and the two units are retractably and detachably combined with each other. In such a combined state, the guide catheter 100 is transendoscopically inserted into a body cavity.

Figure 3:
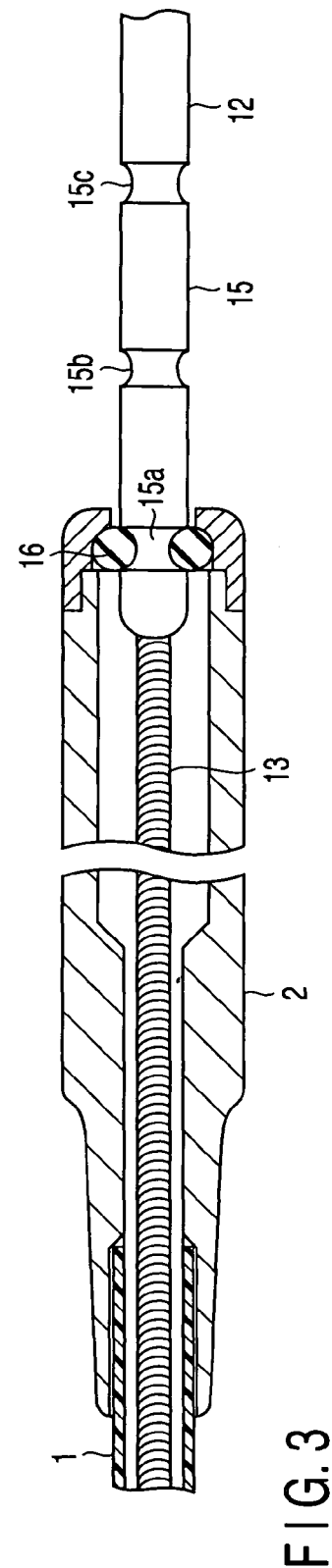
FIG. 3 is a vertical cross-sectional view showing the vicinity of an operator's hand side of the transendoscopic medical instrument according to the first embodiment.

As shown in FIG. 1, the mantle tube unit 101 has a long tube (a sheath) 1 which can be inserted into a channel of an endoscope and has flexibility and a connector 2 which is coupled with a base end of this tube 1. As shown in FIG. 3, the base end portion of the tube 1 is fitted in the end portion of the connector 2, and the both members are connected by mechanically fixing the fitted portion. An inner space (a hole) of the tube 1 communicates with an inner space (a hole) of the connector 2.

Figure 2:
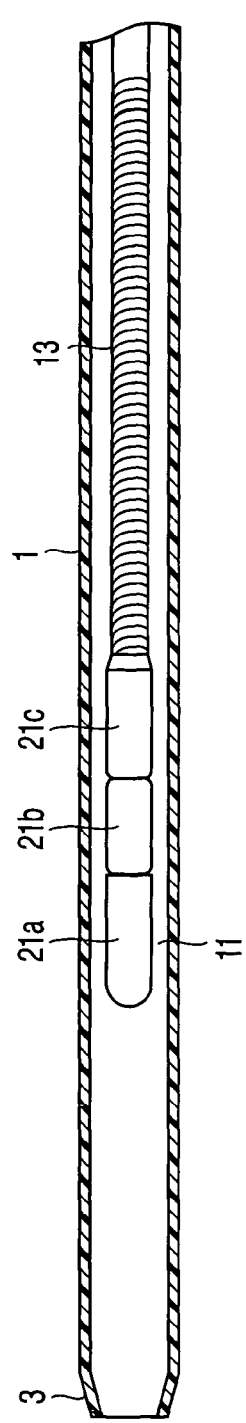
FIG. 2 is a vertical cross-sectional view showing the vicinity of an end portion of the transendoscopic medical instrument according to the first embodiment.

As shown in FIG. 2, the end portion of the tube 1 in the mantle tube unit 101 is formed as a tapered portion 3 having a shape in which inside and outside diameters are tapered. This tapered portion 3 can be elastically expanded when a predetermined pressing force is applied thereto. A wall thickness of the tube 1 is small, and hence the entire tube 1 has a flexible configuration. Even though the tapered portion 3 does not have a shape in which an outer surface is tapered, it is good enough for the tapered portion 3 to have a shape in which an inner surface side is tapered.

As shown in FIG. 2, the guide unit 102 has a configuration in which an end acting portion 11 is mechanically connected with an operation portion 12 which operates the end acting portion 11 through a long metallic sheath 13 comprising, e.g., a coil.

FIGS. 2 and 3 show a relationship when the mantle tube unit 101 is combined with the guide unit 102. As shown in FIG. 3, the operation portion 12 of the guide unit 102 and the sheath 13 are coupled with each other by connecting a base end of the sheath 13 with an end portion of a slider rod 15 extending to the front side from the operation portion 12.

As shown in FIG. 3, a plurality of engagement grooves (concave portions) 15a, 15b and 15c are formed on an outer peripheral surface of the slider rod 15 at predetermined intervals. A convex member 16 provided to protrude toward the inner side is provided in the connector 2 of the mantle tube unit 101. One of the engagement grooves 15a, 15b and 15c of the slider rod 15 is selectively engaged with this convex member 16. As a result, there can be configured means for latching and fixing the mantle tube unit 101 to the guide catheter 100 at a predetermined position.

The convex member 16 is annularly formed of an elastic material or the like. Therefore, the convex portion 16 can slide on the slider rod 15 and can be detachably engaged with the engagement grooves 15a, 15b and 15c. The convex member 16 provided in the mantle tube unit 101 is engaged with one of the engagement grooves 15a to 15c by pushing/pulling the entire operation portion 12. The engagement grooves 15a to 15c determine a first position, a second position and a third position as different stop positions of the guide unit 102 with respect to the mantle tube unit 101. With such a configuration, there can be configured a so-called three-stage click mechanism which can select the three stop positions of the guide unit 102. Each latch portion serves as a plurality of latch parts which hold the insertion instrument with respect to the sheath.

At the engagement stop position shown in FIG. 3, the convex member 16 is engaged with the first engagement groove 15a and, at this moment, the end acting portion 11 provided at the end of the guide unit 102 is pulled into and accommodated in the tube 1 from the end of the tube 1 of the mantle tube unit 101 as shown in FIG. 2. In this pulled/accommodated state, the end acting portion 11 of the guide unit 102 is kept under restraint by an inner wall of the tube 1, and hence it has a straight shape along the tube 1.

Figure 4:
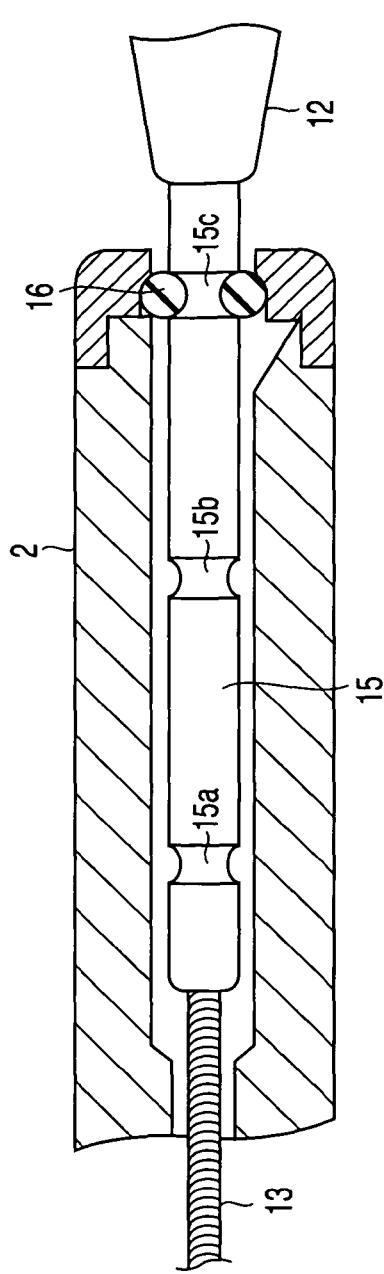
FIG. 4 is a vertical cross-sectional view showing the vicinity of a base end portion of the transendoscopic medical instrument according to the first embodiment in another state.
Figure 5:
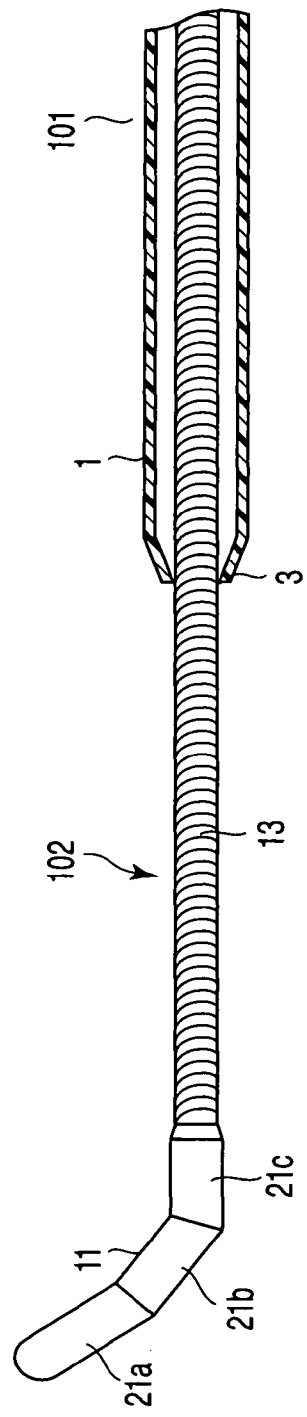
FIG. 5 is a vertical cross-sectional view showing the vicinity of the end portion of the transendoscopic medical instrument according to the first embodiment in another state.

As shown in FIG. 4, in a stop state where the convex member 16 is engaged with the engagement groove 15c positioned on the side closest to an operator's hand side, the end acting portion 11 at the end of the guide unit 102 completely protrudes from the end of the tube 1 as shown in FIG. 5.

Figure 6:
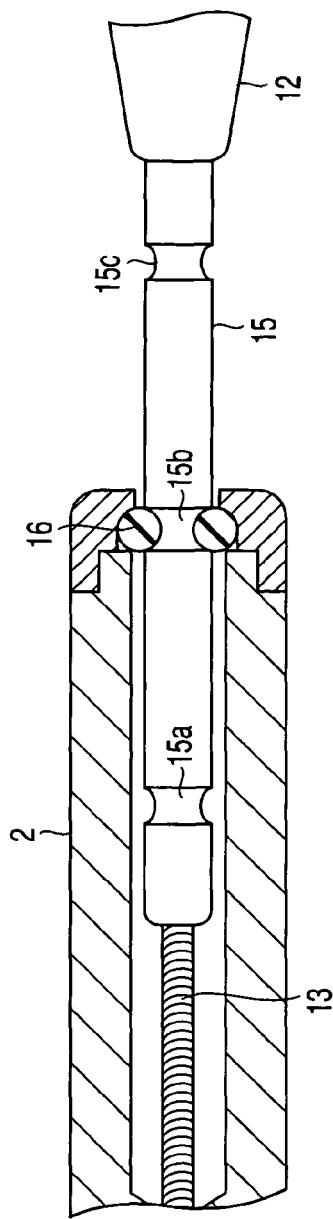
FIG. 6 is a vertical cross-sectional view showing the vicinity of the end portion of the transendoscopic medical instrument according to the first embodiment in still another state.

As shown in FIG. 6, in a stop state where the convex member 16 is engaged with the engagement groove 15b which is placed at the middle position, a part of the end acting portion 11 only in the guide unit 102 slightly protrudes from the end of the tube 1.

The number of the engagement grooves 15a to 15c and the number of installation positions of these grooves are three, and these grooves are provided at equal intervals, but this number and the installation positions may be changed within a range of an allowable length of the slider rod 15.

Figure 8:
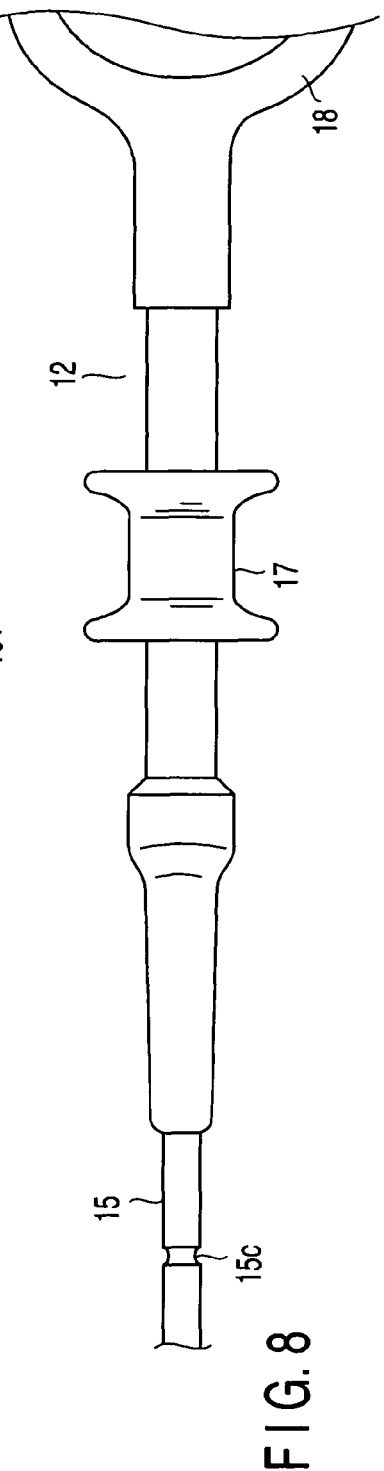
FIG. 8 is a side view of an operation portion in a guide unit of the transendoscopic medical instrument according to the first embodiment.
Figure 9:
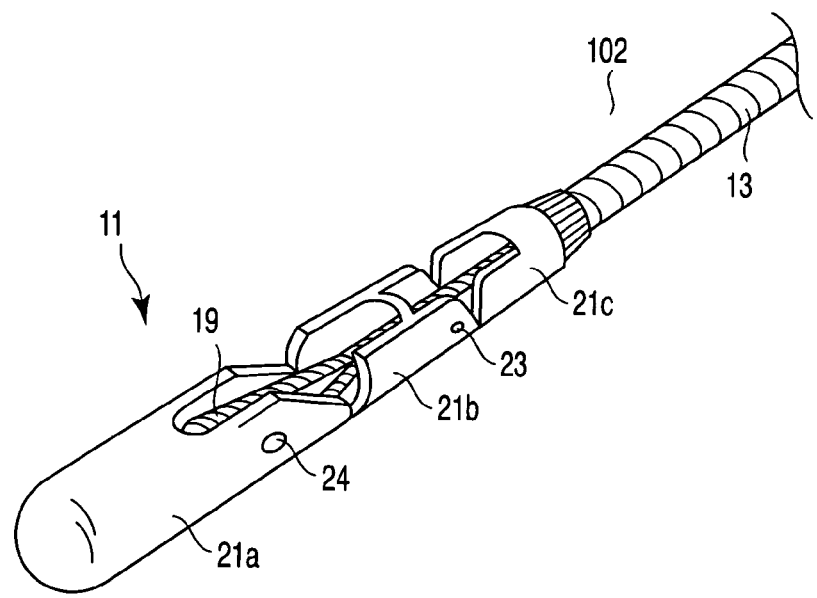
FIG. 9 is a perspective view of an end acting portion in the guide unit of the transendoscopic medical instrument according to the first embodiment.
Figure 10:
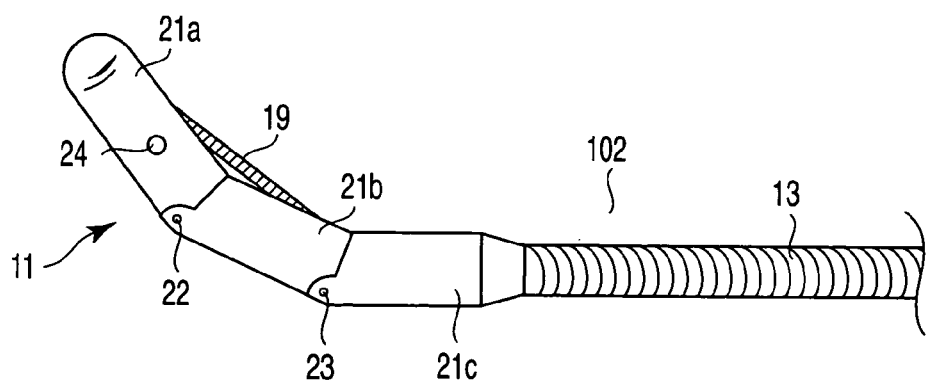
FIG. 10 is a side view of the end acting portion in the guide unit of the transendoscopic medical instrument according to the first embodiment.

As shown in FIG. 8, a slider 17 and a fingerhold ring 18 are provided to the operation portion 12 of the guide unit 102. A base end of a later-described operation wire 19 is coupled with the slider 17. The operation wire 19 is guided to the end through the inside of the sheath 13 and the inside of the slider rod 15. As shown in FIGS. 9 and 10, the end of the operation wire 19 is connected with a movable member of the end acting portion 11 in the guide unit 102.

As shown in FIGS. 9 and 10, the end acting portion 11 of the guide unit 102 is configured by coupling three members, i.e., an end portion 21a whose end portion has a spherical shape, a joint 21b and a base portion 21c in series. The end 21a and the joint 21c are coupled with each other through a spindle pin 22, and the joint 21b and the base portion 21c are coupled with each other through a joining pin 23. As shown in FIG. 10, a position of the spindle pin 22 which pivotally couples the end 21a and the joint 21b and a position of the joining pin 23 which pivotally couples the joint 21b and the base portion 21c are arranged in such a manner that they are biased to the same side with respect to the center of the end acting portion 11. Therefore, the end 21a, the joint 21b and the base portion 21c of the end acting portion 11 constitute a flexible flexure portion which curves toward the opposite side. In this manner, in order to bend the end acting portion 11 toward one side only, each facing edge of the end 21a, the joint 21b and the base portion 21c is obliquely notched. As shown in FIG. 10, when the end acting portion 11 is bent to the maximum, the notched base ends are joined together. As shown in FIGS. 9 and 10, the end surface of the end 21a is formed into a substantially spherical shape in order to alleviate contact with respect to a tissue.

It is to be noted that the hinge portions of the end 21a, the joint 21b and the base portion 21c may be coupled through a deformable thin portion provided between the end 21a and the joint 21b or between the joint 21b and the base portion 21c in place of using the pins 22 and 23 in order to bend the end acting portion 11.

The operation wire 19 inserted into the joint 21b from the inside of the sheath 13 through the base portion 21c and reaches the inside of the end 21a of the end acting portion 11, and a wire end is coupled with a member of the end 21a. A connection pin 24 is provided to the end 21a from side to side. The end of the operation wire 19 is connected to the connection pin 24 by winding the end portion of the operation wire 19 constituting a loop around this connection pin 24 in such a manner that the swiveling movement is allowed without restraint.

When the operation wire 19 is moved forward or backward by pushing/pulling the slider 17 of the operation portion 12 in the front-and-back direction, the end acting portion 11 is bent. A flexible operating means is constituted. That is, as shown in FIG. 10, when the slider 17 is pulled toward the operator's hand side and the end 21a of the end acting portion 11 is pulled by the operation wire 19, the end 21a swivels around the spindle pin 22 with respect to the joint 21b, the joint 21b swivels around the connection pin 23 with respect to the base portion 21c, and the end acting portion 11 is bent. Usually, the end 21a and the joint 21b move in the mentioned order to follow up pulling of the operation wire 19. Finally, as shown in FIG. 10, the end acting portion 11 is bent in a state that the entire end acting portion 11 has a bent shape. The bending (flexure) level can be arbitrary changed depending on a moving distance of the slider 17.

Figure 11:
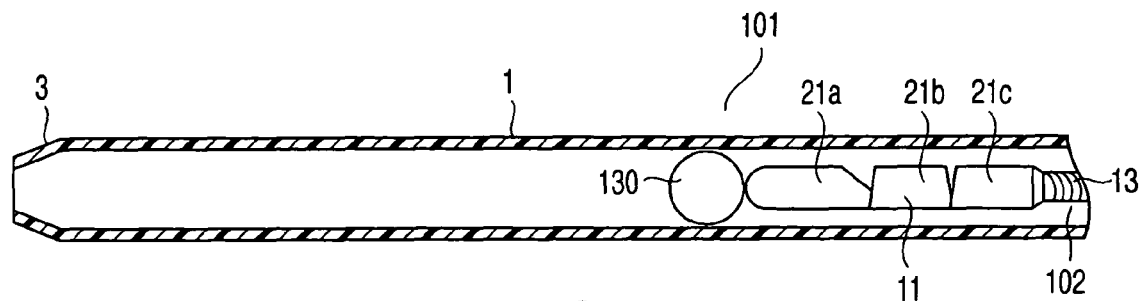
FIG. 11 is a vertical cross-sectional view showing the vicinity of the end portion having a marker member loaded therein in the transendoscopic medical instrument according to the first embodiment.

In a case where an x-ray marker is placed and kept in a body cavity, as shown in FIG. 11, an in-vivo indwelling spherical marker member 130 formed of a radiopaque material is inserted into the tube 1, and the guide unit 102 is inserted and arranged at a position on the rear side of the marker member 130. At this time, the spherical marker member 130 is latched by the tapered portion 3 at the end of the tube 1 so that it does not readily bounce out from the end of the tube 1.

It is possible to keep the x-ray maker at or in the vicinity of a diseased part in a bronchial tube which an endoscope cannot reach, or obtain a tissue or a cell from a part in a body cavity by using the endoscope guide catheter 100 according to this embodiment.

A description will now be given as to how to use this guide catheter.

When placing and keeping the x-ray marker at or in the vicinity of a diseased part in a bronchial tube which the endoscope cannot reach, the guide unit 102 is first inserted through a channel of the endoscope on x-rays, and the guide unit 102 alone is led to a corresponding part. At this time, the operation portion 12 of the guide unit 102 is pushed into the mantle tube unit 101 as shown in FIG. 4 so that the end acting portion 11 of the guide unit 102 completely protrudes from the end of the tube 1 as shown in FIG. 5.

Figure 14:
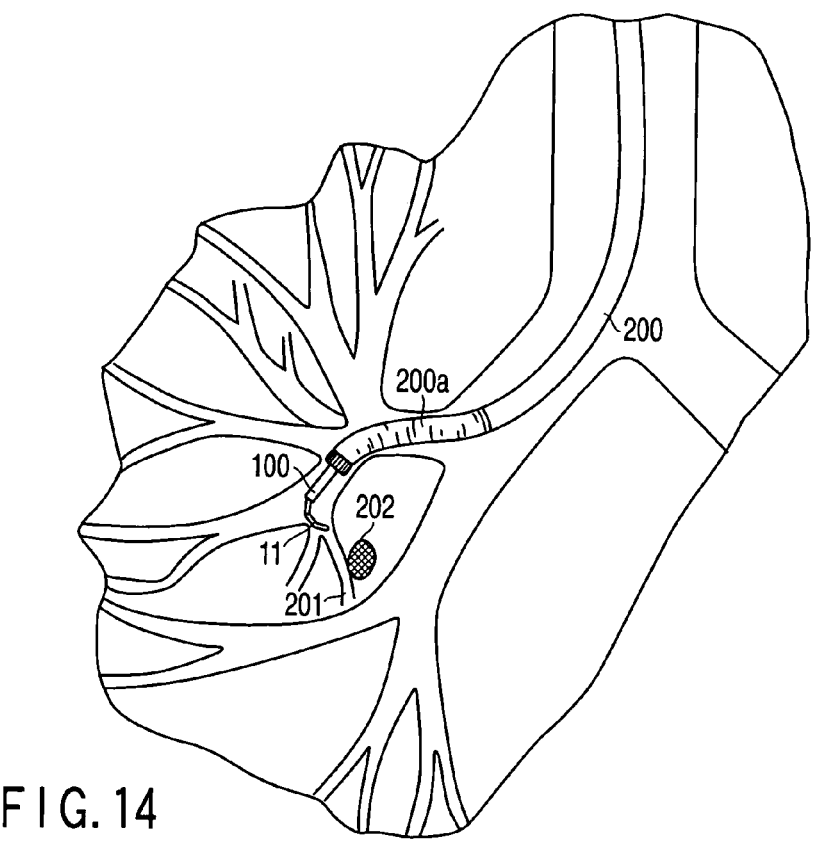
FIG. 14 is an explanatory drawing when the transendoscopic medical instrument according to the first embodiment is guided to or near a diseased part in a bronchial tube which an endoscope cannot reach.

In this state, as shown in FIG. 14, the guide catheter 100 is inserted into a body cavity through a treatment instrument channel of the endoscope. The guide catheter 100 alone protrudes from the end of the insertion portion of the endoscope 200, and the guide catheter 100 is moved forward in the body cavity on x-rays. At this time, in the operation portion 12 of the guide unit 102, the end acting portion 11 of the guide unit 102 is appropriately bent (curved) while pushing and pulling the slider 17, a bronchial branch 201 to which the end acting portion should be guided is selected, and the end acting portion 11 is pushed forward in the tracheal branch 201. At this time, a position and a direction of the end of the insertion portion may be also selected by bending a flexure portion 200a in the insertion portion of the endoscope 200.

Figure 15:
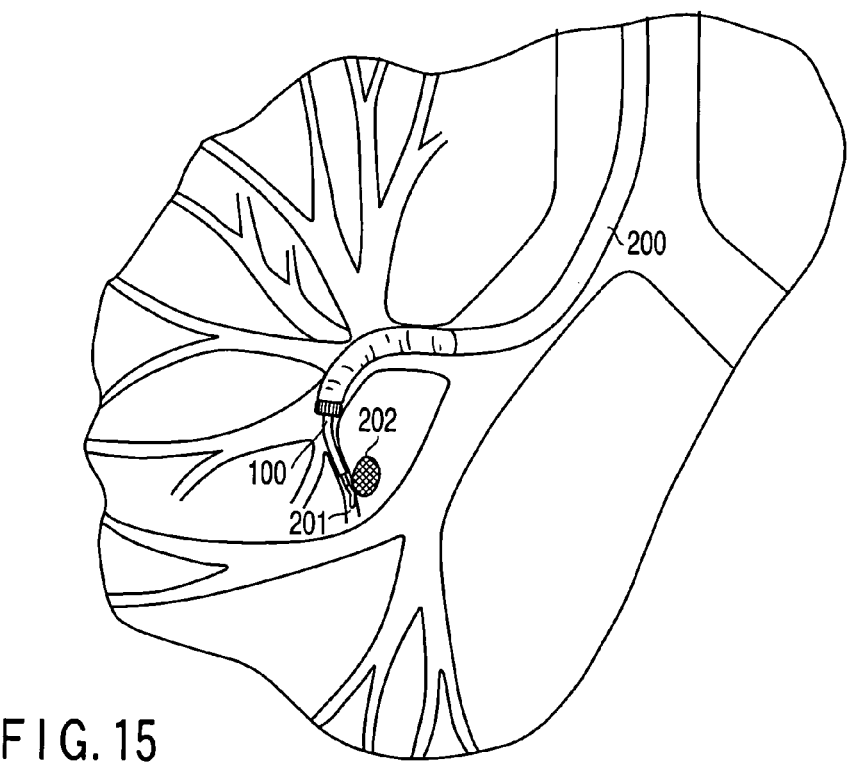
FIG. 15 is an explanatory drawing when the transendoscopic medical instrument according to the first embodiment is guided to or near a diseased part in a bronchial tube which an endoscope cannot reach.

Here, as shown in FIG. 15, when a diseased part 202 is specified by using x-rays, the end acting portion 11 of the guide unit 102 is pushed forward to the vicinity of the diseased part 202 while bending the end acting portion 11. By doing so, the guide unit 102 is guided to a diseased part or the like existing in a bronchial tube, especially a peripheral bronchial tube cavity by the bending function of the flexible end acting portion 11, and the tube 1 of the catheter 100 can be guided to a diseased part of the like through this guide unit 102.

Figure 16:
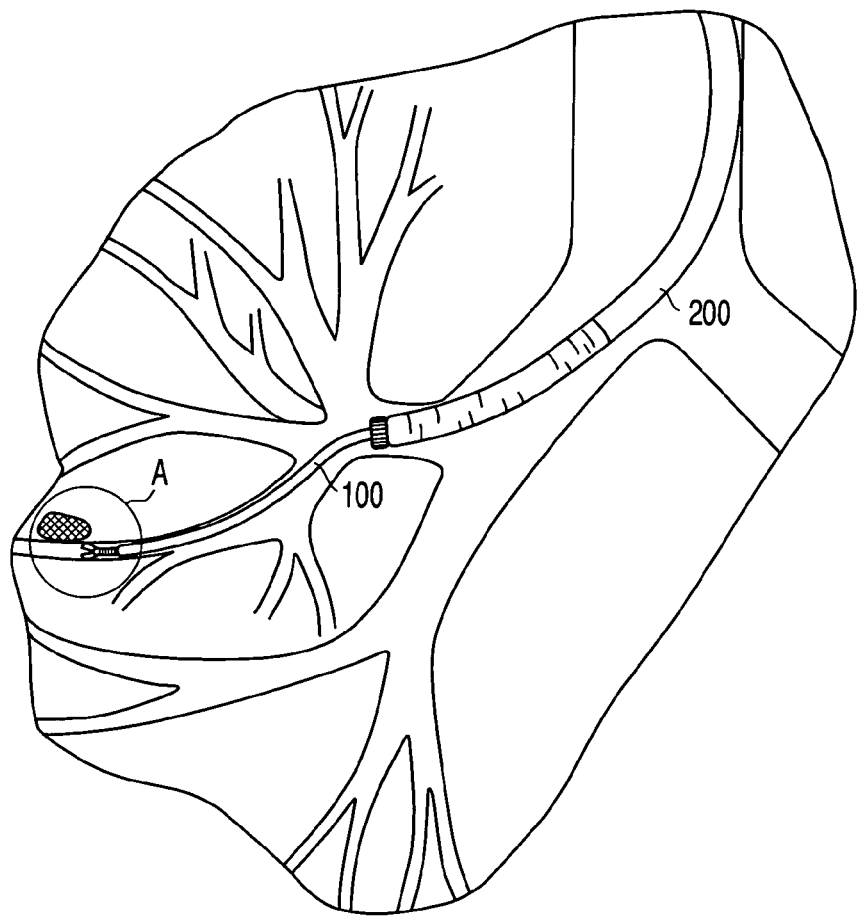
FIG. 16 is an explanatory drawing when a biopsy is performed by guiding the transendoscopic medical instrument according to the first embodiment to or near a diseased part in a bronchial tube which an endoscope cannot reach.
Figure 17:
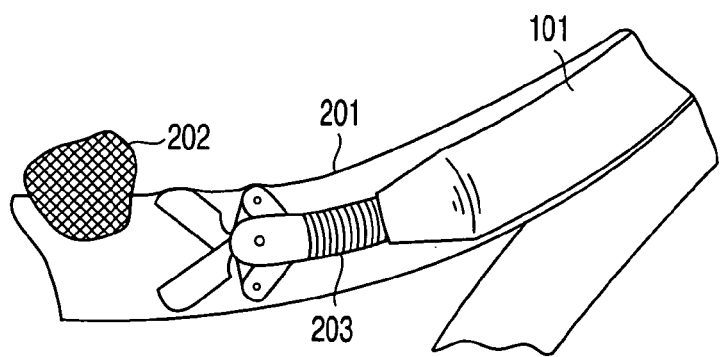
FIG. 17 is an enlarged view of a portion A in FIG. 16.

Further, as shown in FIGS. 16 and 17, in the case of obtaining a tissue of the diseased part 202 after reaching a target position, the guide unit 102 as a first transendoscopic insertion instrument is completely removed from the mantle tube unit 101, a second transendoscopic insertion instrument, e.g., an endoscopic treatment instrument 203 as a bioptome is inserted, and a tissue of the diseased part 202 can be consequently obtained as shown in FIG. 17 so that the obtained tissue is subjected to a diagnosis.

Here, as shown in FIGS. 16 and 17, although the description has been given as to the example in which the endoscopic treatment instrument 203 is determined as a bioptome, this second transendoscopic treatment instrument can be an instrument which is in an inner space allowable range of the mantle tube unit 101 as a transendoscopic sheath, e.g., a cytological diagnosis item such as a cytologic brush, a curet or an aspiration biopsy needle or a high-frequency treatment instrument, and the type of transendoscopic item are not restricted.

Figure 12:
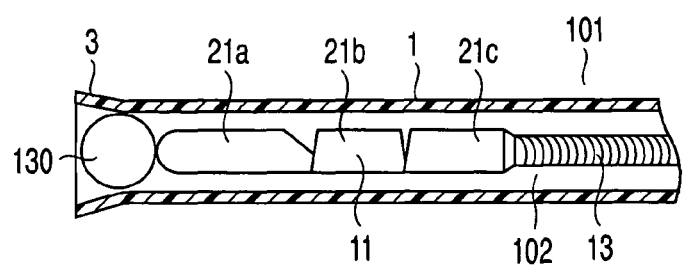
FIG. 12 is a vertical cross-sectional view showing the vicinity of the end portion when pushing out the marker member in the transendoscopic medical instrument according to the first embodiment.
Figure 18:
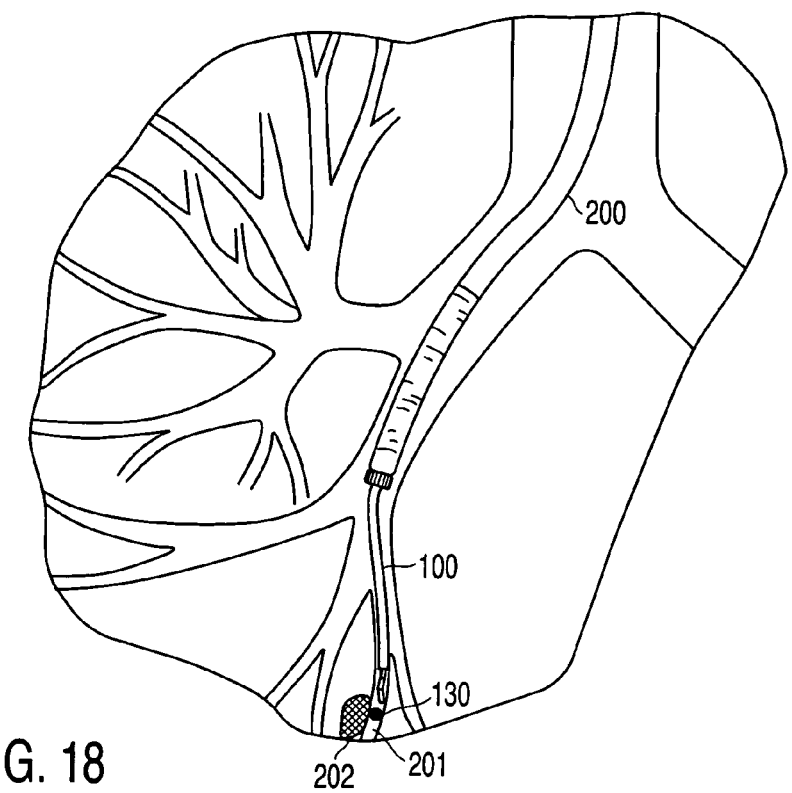
FIG. 18 is an explanatory drawing when the transendoscopic medical instrument according to the first embodiment is guided to or near a diseased part in a bronchial tube which an endoscope cannot reach, and a marker is placed and kept.

A description will now be given as to an example where the marker detention of the like is performed. In this case, as described above, a spherical marker member 130 is loaded in the tube 1 of the mantle tube unit 101 in advance as shown in FIG. 11, the tube 1 of the mantle tube unit 101 is led to a desired bronchial branch 201, and the guide unit 102 is then gradually pushed forward as shown in FIG. 12 so that the spherical marker member 130 is pushed out and emitted to the bronchial branch 201 (see FIG. 18). Here, since the tube 1 is configured to have a small wall thickness, the spherical marker member 130 can be withdrawn from the mantle tube unit 101 while expanding and deforming the tapered portion 3 formed at the end, thereby discharging the spherical marker member 130 into a body cavity as shown in FIG. 18. The guide unit functions as a slidable and detachable pusher element which pushes out the marking member from the mantle tube unit.

Figure 13:
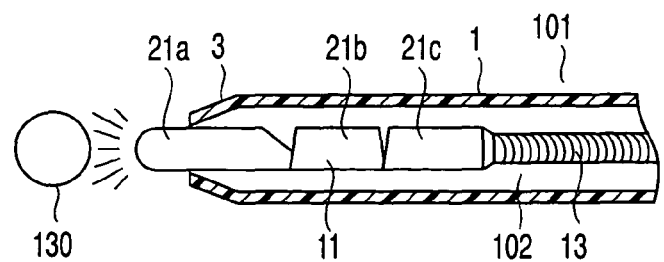
FIG. 13 is a vertical cross-sectional view showing the vicinity of the end portion when discharging the marker member in the transendoscopic medical instrument according to the first embodiment.

At this time, as shown in FIG. 6, the engagement groove 15b of the slider rod 15 is stopped at a position where the engagement groove 15b can be engaged with the convex member 16 of the mantle tube unit 101. At this position, as shown in FIG. 13, the spherical marker member 130 is completely withdrawn from the mantle tube unit 101, and the spherical marker member 130 can be fitted and kept in a body cavity which is a peripheral bronchial cavity in this example as shown in FIG. 18.

The catheter can be assuredly guided to a diseased part or the like which exists in a bronchial cavity, especially a complicated peripheral bronchial cavity by the flexible end acting portion 11 of the guide unit 102. A diagnostic treatment of a diseased part can be assuredly performed by replacing the guide unit 102 as the first endoscope insertion instrument with a treatment instrument as a second endoscope insertion instrument for a diagnosis or a treatment with respect to the catheter led to a target position. Furthermore, the marker member 130 can be assuredly kept at the target position.

Second Embodiment

Figure 19:
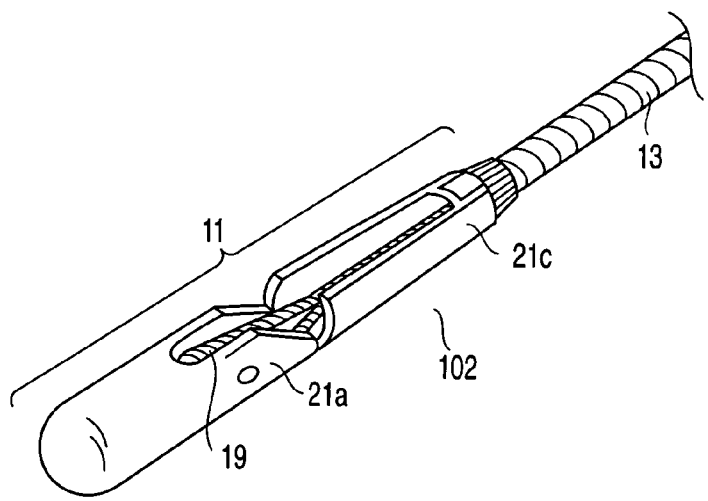
FIG. 19 is a perspective view of an end acting portion in a guide unit of a transendoscopic medical instrument according to a second embodiment of the present invention.
Figure 20:
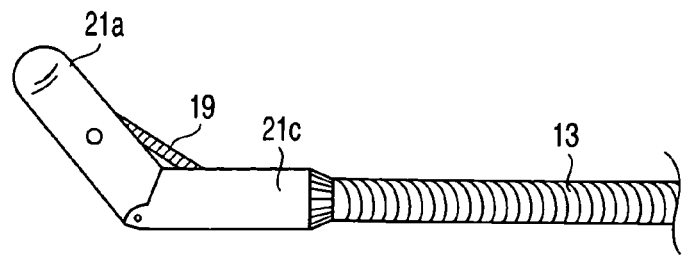
FIG. 20 is a side view showing the vicinity of the end acting portion in the guide unit of the transendoscopic medical instrument according to the second embodiment.

This embodiment is different from the abovedescribed first embodiment in the configuration of the end acting portion 11 in the guide unit 102. That is, as shown in FIGS. 19 and 20, the two members, i.e., the end 21a and the base portion 21c constitute the end acting portion 11. The other structures are the same as those in the above-described first embodiment.

By pulling the slider 17 of the operation portion 12 like the first embodiment, the operation wire 19 is pulled, and the end action portion 11 has a bent shape as shown in FIG. 20. Other effects and advantages are the same as the effects and advantages of the first embodiment mentioned above.

Third Embodiment

In this embodiment, the shape of the end 21a constituting a part of the end acting portion 11 of the guide unit 102 is constituted as shown in FIGS. 21 and 22. That is, the end 21a is constituted of a member having a substantially columnar shape, a cone-shaped concave portion 40 which is deep at the center is provided to this end surface portion, and a rim portion 41 of the concave portion 40 is formed into a round shape. In this example, the cone-shaped concave portion 40 is constituted in such a manner that the spherical marker member 130 can be stably supported. Other structures are the same as those of the first embodiment and the second embodiment.

In this embodiment, when placing and keeping the marker in a body cavity, the spherical marker member 130 is held in a state where the spherical marker member 130 falls in the concave portion 40 of the end 21a. Therefore, when placing and keeping the marker member 130 in the target position in a body cavity, the marker member 130 can be assuredly pushed out from the tube 1 in a further stable state. Other effects and advantages are the same as the effects and advantage of the first embodiment and the second embodiment.

Fourth Embodiment

Figure 24:
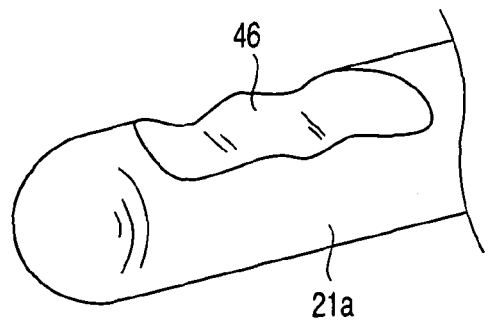
FIG. 24 is a perspective view of an end portion which is of another type in the guide unit of the transendoscopic medical instrument according to the fourth embodiment of the present invention.

In this embodiment, the end 21a which is a constituent of the end acting portion 11 of the guide unit 102 is formed into a substantially columnar shape at an end as shown in FIG. 23, and a flat portion 45 is formed at a part of the end 21a in the longitudinal direction. Furthermore, as shown in FIG. 24, the part of the flat portion 45 may be formed like an undulating surface 46.

According to this embodiment, when performing selective insertion with respect to a bronchial branch, the end acting portion 11 can be readily hooked in a bronchial cavity of the branch portion. This also leads to a reduction in time required for the catheter to reach a target position.

Other configurations are the same as the first and second embodiments. In this embodiment, the same effects and advantages as those of the first and second embodiments can be obtained.

Fifth Embodiment

Figure 25:
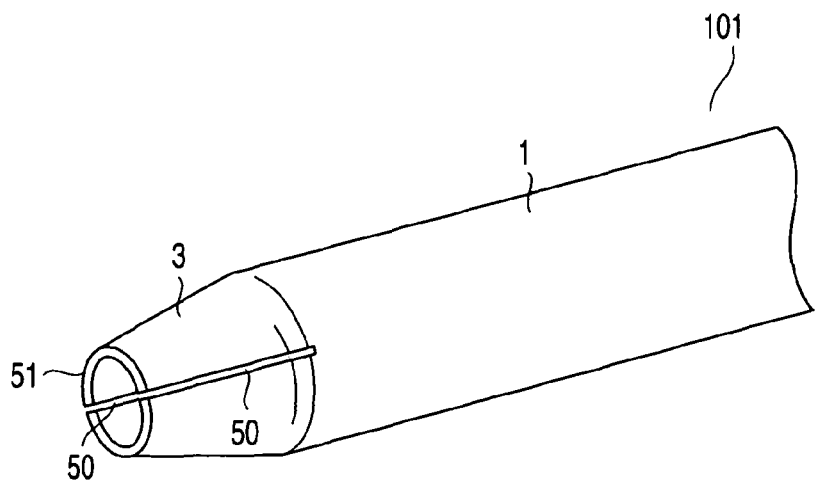
FIG. 25 is a vertical cross-sectional view of an end portion of a transendoscopic medical instrument according to a fifth embodiment of the present invention.

In this embodiment, as shown in FIG. 25, in the mantle tube unit 101, at least one slit 50 is additionally continuously provided from an opening end 51 of the tube 1 to the tapered portion 3 provided at the end of the tube 1 with a length comparable to the tapered portion 3. Other structures are the same as the first to fourth embodiments. Here, the two slits 50 are symmetrically formed on one plane.

Figure 26:
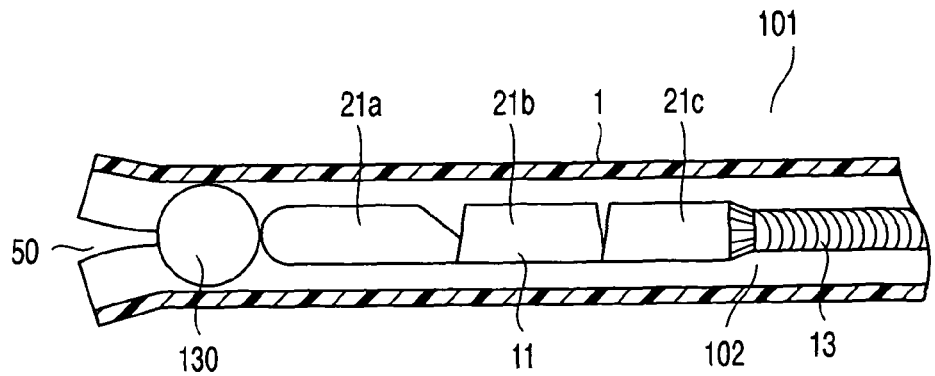
FIG. 26 is a vertical cross-sectional view of the end portion of the transendoscopic medical instrument according to the fifth embodiment.

In this embodiment, as shown in FIG. 26, when withdrawing the spherical marker member 130 from the mantle tube unit 101, the slit 50 is split so that the spherical marker member 130 protrudes. Therefore, the spherical marker member 130 can readily protrude and be discharged from the opening end 51. Other structures are the same as those of first to fourth embodiments.

According to this embodiment, when pushing out the marker member 130 from the catheter, the marker member 130 can be caused to protrude by using a lighter force. Moreover, when the endoscope insertion instrument is replaced in the mantle tube unit 101, protrusion of this insertion instrument can be easily performed.

Sixth Embodiment

As shown in FIG. 27, this embodiment has a configuration in which a target to which the convex member 16 in the configuration of the first embodiment is changed from the connector 2 to the slider rod 15 and depressions of the three engagement grooves 12*a*, 12*b* and 12*c* to which the convex member 16 is latched are formed at predetermined intervals on an inner wall 2*e* forming an inner space 2*d* of the connector 2.

The convex member 16 is provided to the slider rod 15 constituted on the front side of the operation portion 104 of the guide unit 102. Additionally, the convex member 16 is formed of an elastic material or the like, and can be detachably closely fitted to a concave portion 15*d* provided to the slider rod 15.

An inner taper 2*g* which facilitates insertion of the convex member 16 is formed in an opening end portion 2*f* of the connector 2. Other structures are the same as those of the first embodiment.

Figure 7:
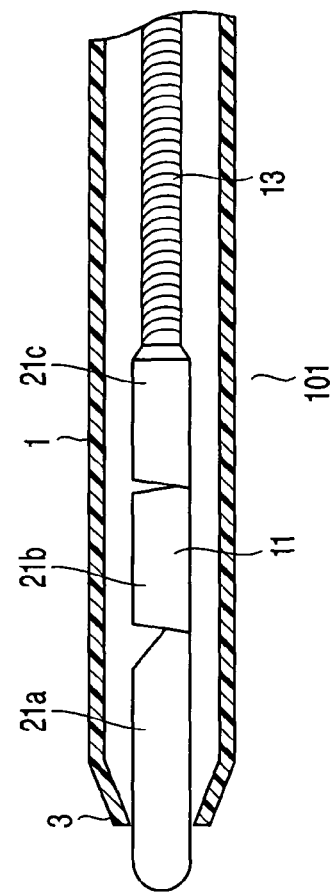
FIG. 7 is a vertical cross-sectional view showing the vicinity of the end portion of the transendoscopic medical instrument according to the first embodiment in yet another state.

In FIG. 27, the convex member 16 is engaged with the engagement groove 12*c* and, at this time, a relative positional relationship between the mantle tube unit 101 and the guide unit 102 on the end side is in a state shown in FIG. 2. Further, a state shown in FIG. 7 is provided when the convex member 16 is engaged with the engagement groove 12*b*, and a state shown in FIG. 5 is realized when the convex member 16 is engaged with the engagement groove 12*a*.

It is to be noted that the engagement grooves 12*a*, 12*b* and 12*c* are not restricted to the example where these grooves are provided at the three positions, and the plurality of grooves may be formed as long as a length of the inner wall 2*e* forming the inner space 2*d* of the connector 2 allows.

Other effects of this embodiment are the same as those of the first to fifth embodiments. Furthermore, the advantage of this embodiment is the same as the first embodiment and the second embodiment and, in addition to this advantage, the convex member 16 can be replaced with a new member when the function of the convex member 16 is deteriorated due to abrasions/damages.

It is to be noted that the present invention is not restricted to each of the foregoing embodiments. According to the above explanation, the following matters can be obtained.

As described above, since there is provided the configuration in which the long guider whose end performs flexural operations is both slidable and detachable in the long outer tube in combination, the present invention can be selectively pushed forward in complicated bronchial branches, thereby realizing insertion into a target part of a peripheral bronchial tube.

After reaching a desired position of, e.g., a diseased part, when the guider is removed while keeping the outer tube, another endoscopic forceps or the like for use in, e.g., diagnosis can be again inserted into the outer tube. Furthermore, when the end of the outer tube is placed at a desired part, a tissue, a cell or the like can be assuredly obtained by using a reinserted forceps or the like. Moreover, in cases where the marker member is detained, a role of a pusher which pushes out the marker member can be realized by loading the marker member in the outer tube after removal of the guider and again inserting the guider.

Selective insertion to a complicated part such as a bronchial branch is possible, insertion into such a part can be assuredly/rapidly performed, and a diagnosis, a treatment or the like which is performed successively after this insertion can be also assuredly/rapidly realized. The x-ray marker member can be also readily retained at a predetermined position. Since there is provided the configuration in which the long guider whose end performs flexural operations is both slidable and detachable in the long outer tube in combination, the present invention can be selectively pushed forward in a complicated bronchial branch, thereby realizing insertion to a target part of a peripheral bronchial tube. By removing the guider while keeping the outer tube after reaching a desired position of, e.g., a diseased part, another endoscopic forceps for a diagnostic application or the like can be again inserted into the outer tube. When the end of the outer tube is placed at a desired part, a tissue, a cell or the like can be assuredly obtained by using the reinserted forceps or the like. Even if the marker member is retained, a role of a pusher which pushes out the maker member can be realized by loading the marker member in the outer tube after removal of the guider and again inserting the guider.

What is claimed is:

1. A transendoscopic medical instrument comprising:
an x-ray marker member formed of a radiopaque material;
a sheath having a distal end, a proximal end and an internal space between the distal end and the proximal end, the sheath being configured to insert the x-ray marker member into the internal space from a proximal side of the sheath and the sheath including a distal end opening portion in which an inner diameter is reduced from a proximal side of the distal end to a tip end at the distal end of the sheath;
a guide unit which is configured to be inserted into the internal space of the sheath, which includes a flexible elongated member and a bendable distal end action portion connected to a distal part of the flexible elongated member, the bendable distal end action portion including a tip end portion, a base portion and a joint between the tip end portion and the base portion, and
the bendable distal end action portion being configured to push the x-ray marker member to a distal side of the sheath, being configured to be protruded with respect to the distal end opening portion of the sheath and being configured to guide the sheath; and
a latch portion which is configured to latch the guide unit with respect to the sheath at a predetermined position and which includes;
a first latch part which latches the guide unit at a first position where the x-ray marker member and the whole bendable distal end action portion of the guide unit are housed in the internal space of the sheath;
a second latch part which latches the guide unit at a third position where the sheath can be guided to a target region by fully protruding the base portion of the bendable distal end action portion and a part including the distal part of the flexible elongated member of the guide unit from the distal end opening portion of the sheath; and a third latch part which latches the guide unit at a second position where the x-ray marker member is placed and kept at a position to which at least a part including the tip end portion is protruded to the distal end opening portion of the sheath, and at least a part including the base end portion is housed into the internal space of the sheath.

2. The transendoscopic medical instrument according to claim 1, wherein the joint of the bendable distal end action portion of the guide unit comprises a plurality of pivot members from the tip end portion toward the base portion of the bendable distal end action portion, and when the bendable distal end action portion of the guide unit is located at the second position, one of the plurality of pivot members which is the closest to the distal end of the bendable distal end action portion is on the proximal end side compared with the distal end of the sheath.

3. The transendoscopic medical instrument according to claim 1, wherein at least one slit is formed at the distal end of the sheath.

4. The transendoscopic medical instrument according to claim 1, wherein a tip end portion of the distal end action portion of the guide unit is formed into a substantially spherical surface.

5. The transendoscopic medical instrument according to claim 1, wherein an outer diameter of the distal end opening of the sheath is tapered from the proximal side to the distal side.

6. The transendoscopic medical instrument according to claim 1, wherein the bendable distal end action portion is able to be bent toward one side.

7. The transendoscopic medical instrument according to claim 1, wherein the tip end portion has a spherical shape, the tip end portion and the joint are coupled with each other through a spindle pin, and the joint and the base portion are coupled with each other through a joining pin.

* * * * *